(12) United States Patent
Lee et al.

(10) Patent No.: US 6,617,478 B2
(45) Date of Patent: Sep. 9, 2003

(54) PROCESS FOR PREPARING A 1,3-ALKANDIOL FROM 3-HYDROXYESTER

(75) Inventors: Byeong No Lee, Seoul (KR); In Sun Jung, Daejun-Shi (KR); Eun Joo Jang, Daejun-Shi (KR); Jung Ho Lee, Daejun-Shi (KR); Hyung Rok Kim, Daejun-Shi (KR); Yo Han Han, Daejun-Shi (KR)

(73) Assignees: Samsung Electronics Co., Ltd., Kyungki-do (KR); Korea Research Institute of Chemical Technology, Kaejun-shi (KR)

( * ) Notice: Subject to any disclaimer, the term of this patent is extended or adjusted under 35 U.S.C. 154(b) by 0 days.

(21) Appl. No.: 10/212,671

(22) Filed: Aug. 6, 2002

(65) Prior Publication Data

US 2003/0069456 A1 Apr. 10, 2003

Related U.S. Application Data

(63) Continuation-in-part of application No. 09/995,798, filed on Nov. 29, 2001.

(30) Foreign Application Priority Data

Nov. 29, 2000 (KR) .......................... 2000-71643
Nov. 1, 2001 (KR) ....................... 2001-067901
Jun. 13, 2001 (KR) ....................... 2001-33142

(51) Int. Cl.[7] .................. C07C 27/00; C07C 27/04; C07C 31/18; C07C 29/00
(52) U.S. Cl. ........................... 568/864; 568/861
(58) Field of Search ................. 568/864, 861

(56) References Cited

U.S. PATENT DOCUMENTS

| | | | |
|---|---|---|---|
| 4,440,873 A | 4/1984 | Miyazaki et al. | 502/244 |
| 4,443,649 A | 4/1984 | Jones et al. | 585/500 |
| 4,511,744 A | 4/1985 | Miyazaki et al. | 568/864 |
| 4,929,777 A | 5/1990 | Irick et al. | 568/864 |
| 4,973,769 A | 11/1990 | Mueller et al. | 568/864 |
| 5,093,537 A | 3/1992 | Unrub et al. | 568/862 |
| 5,185,476 A | 2/1993 | Gustafson | 568/831 |
| 5,406,004 A | 4/1995 | Eastland et al. | 568/831 |
| 5,723,389 A | 3/1998 | Slaugh et al. | 468/862 |
| 5,731,478 A | 3/1998 | Slaugh | 568/862 |
| 5,770,776 A | 6/1998 | Powell et al. | 568/862 |
| 5,777,182 A | 7/1998 | Powell | 568/862 |
| 5,821,092 A | 10/1998 | Nagarajan | 435/158 |
| 6,013,494 A | 1/2000 | Nakamura | 435/158 |
| 6,136,576 A | 10/2000 | Diaz-Torres | 435/158 |
| 6,140,543 A | 10/2000 | Brossmer et al. | 568/458 |
| 6,191,321 B1 | 2/2001 | Forschner et al. | 568/864 |
| 6,232,511 B1 | 5/2001 | Haas | 568/862 |

FOREIGN PATENT DOCUMENTS

| | | |
|---|---|---|
| DE | 3734764 | 5/1989 |
| EP | 0361082 | 4/1990 |
| EP | 0373946 | 6/1990 |
| EP | 0577972 | 1/1994 |
| WO | 99/38613 | 8/1999 |
| WO | 00/18712 | 4/2000 |

*Primary Examiner*—Johann Richter
*Assistant Examiner*—Elvis O. Pice
(74) *Attorney, Agent, or Firm*—Lee & Sterba, P.C.

(57) ABSTRACT

A process for preparing a 1,3-alkandiol from a 3-hydroxyester, comprises preparing a catalyst by adding an alkaline precipitator to an aqueous copper salt solution to form copper hydroxide particles, and aging the particles following the addition of a colloidal silica thereto; activating the catalyst by reduction with a $H_2$ gas or a $H_2$-containing gas and applying a pressure of about 5 psig to about 2000 psig at a temperature of about 100° C. to about 250° C. in the presence of an activation solvent; and hydrogenating a 3-hydroxyester in a liquid phase slurry with a $H_2$ gas or a $H_2$-containing gas and applying a pressure of about 50 psig to about 3000 psig at a temperature of about 100° C. to about 250° C. in the presence of the activated catalyst and a reaction solvent, whereby a 1,3-alkanediol can be selectively prepared from a 3-hydroxyester with a high yield.

16 Claims, No Drawings

PROCESS FOR PREPARING A 1,3-ALKANDIOL FROM 3-HYDROXYESTER

REFERENCE TO RELATED PATENT APPLICATION

This application is a continuation-in-part of U.S. patent application Ser. No. 09/995,798, filed Nov. 29, 2001, entitled "PROCESS FOR PREPARING 1,3-ALKANEDIOLS FROM 3-HYDROXYESTERS."

BACKGROUND OF THE INVENTION

1. Field of the Invention

The present invention relates, in general, to a process for preparing a 1,3-alkandiol from a 3-hydroxyester. Specifically, the invention relates to a process for preparing a 1,3-alkandiol from a 3-hydroxyester in a liquid phase slurry manner with high yield and selectivity.

2. Description of the Related Art 1,3-alkandiols have been widely used as coating materials and intermediates for various organic syntheses, as well as for raw materials for the production of polyesters. At present, several process are known for preparing 1,3-alkandiols. For example, processes for preparing a 1,3-alkandiol by first hydroformylating an epoxide into a 3-hydroxyaldehyde derivative, and then hydrogenating the 3-hydroxyaldehyde derivative have been proposed (see: U.S. Pat. Nos. 5,770,776; 5,723,389; 5,731,478; and 5,777,182, the disclosures of which are incorporated by reference herein in their entirety). Alternatively, processes for preparing a 1,3-alkandiol by hydrating acrolein into 3-hydroxypropanal, followed by hydrogenation of the 3-hydroxypropanal, also have been proposed (see: U.S. Pat. Nos. 6,232,511 and 6,140,543, the disclosures of which are incorporated by reference herein in their entirety). Other methods have been disclosed that provide 1,3-alkandiols through a certain biological reaction, wherein glycerol is used as a starting material (see: U.S. Pat. Nos. 6,136,576; 6,013,494; and 5,821,092, the disclosures of which are incorporated by reference herein in their entirety).

Commercially, Shell Co. (Louisiana, U.S.A.) succeeded in producing 1,3-propandiol through hydrogenation of 3-hydroxypropanal resulting from the hydroformylation of ethylene oxide. However, the processes in which 3-hydroxyaldehyde or derivatives thereof, such as 3-hydroxypropanal, are generated as intermediates are disadvantageous in that these intermediates are so unstable that they likely will oligomerize themselves or be converted into other side products including acetals. Accordingly, hydrogenation thereof into corresponding 1,3-alkanediols often is not properly completed, and consequently, the quality of the final product is deteriorated.

Even though an alternative process was suggested, wherein a 1,3-alkandiol was prepared by carboesterifying an epoxide with carbon monoxide and an alcohol to produce a 3-hydroxyester, and then hydrogenating the ester group of the 3-hydroxyester, it has not been put to practical use in the industrial field. This is due to primarily to the fact that the reaction pathway is very unselective for 1,3-alkandiols when a conventional hydrogenation catalyst, such as copper-chromium oxide, copper-zinc oxide or Raney nickel, is used. Typically, hydrogenation of hydroxyester compounds having a hydroxyl group at a non-β position, which is involved in, for example, synthesis of 1,4-butanediol or ethyleneglycol, can readily be accomplished with high selectivity and yield because side products resulting from dehydration are produced in minor amounts. On the other hand, β-hydroxyester compounds including 3-hydroxyesters are likely to undergo dehydration reaction resulting in undesired side products.

While a number of Cu- or noble metal-containing catalysts have been studied and developed for use in preparing alcohols from their corresponding carbonyl group-containing compounds, particularly from esters, there have been reported few catalytic processes useful for preparing 1,3-alkandiols from 3-hydroxyesters having a hydroxyl group at the specific β-position. WO 00/18712 and U.S. Pat. No. 6,191,321, the disclosures of which are incorporated by reference herein in their entirety, disclose the use of a Cu/ZnO-based catalyst in preparation of 1,3-propandiol in the presence of an alcohol solvent such as methanol. While the alcohol solvent is helpful to suppress the self-lactonization and degradation of the reactant, 3-hydroxyesters, an alcohol with low boiling point is unfavorable because it cannot maintain high selectivity at a high conversion rate, and because it cannot maintain prolonged reaction stability of the catalyst under $H_2$ gas flow in a fixed-bed catalyst reactor. Moreover, the reactant, 3-hydroxyester, is not much different from the product, 1,3-alkandiol, in chemical properties and boiling point, which makes it difficult to isolate and purify the product from the reactant in the case of a low conversion rate.

Meanwhile, we proposed a process for preparing a 1,3-alkandiol from a 3-hydroxyester in a gas phase or liquid-gas phase manner, by the use of a $CuO/SiO_2$-based catalyst that was shaped into nano-particles with a diameter of about 4 to about 10 nm (see: Korean Patent Application No. 2000-71643). According to the process, 1,3-alkandiols can be obtained with relatively high selectivity owing to high catalytic activity. However, it is difficult to increase the selectivity for 1,3-alkandiols to over 90% using this process, and generation of lactone and other side products with high boiling point likely occurs when the concentration of the reactant is high. Furthermore, the stability of the catalyst may be affected by possible degradation occurring in the course of reduction of the catalyst.

The description herein of certain disadvantages and inefficiencies of materials, processes and apparatus of the related art is in no way intended to limit the invention to embodiments that do not include these materials, processes and apparatus. Indeed, embodiments of the invention may incorporate the disclosed materials, processes and apparatus without suffering from the disclosed disadvantages and inefficiencies.

SUMMARY OF THE INVENTION

A feature of an embodiment of the present invention is to solve the above-mentioned problems of the related art, and to provide a novel process for preparing a 1,3-alkandiol from a 3-hydroxyester. It is a feature of the invention to increase the selectivity for 1,3-alkanediols to 90% or more, as well as to prolong the stability of the catalyst.

In accordance with these and other features of various embodiments of the invention, there is provided a process for preparing a 1,3-alkandiol from a 3-hydroxyester, comprising:

preparing a catalyst by adding an alkaline precipitator to an aqueous copper salt solution to form copper hydroxide particles, and ageing the particles following the addition of a colloidal silica thereto;

activating the catalyst through reduction with $H_2$ gas or $H_2$-containing gas and applying a pressure of about 5 psig to about 2000 psig at a temperature of about 100° C. to about 250° C. in the presence of an activation solvent; and hydrogenating a 3-hydroxyester in a liquid phase slurry with $H_2$ gas or $H_2$-containing gas by applying a pressure of about 50 psig to about 3000 psig at a temperature of about 100° C. to about 250° C. in the presence of the activated catalyst and a reaction solvent to prepare a 1,3-alkandiol.

All of the above features and other features of the present invention may be successfully achieved and will be readily apparent to those skilled in the art from the detailed description that follows.

DETAILED DESCRIPTION OF THE INVENTION

Priority Korean Patent Application Nos. 2000-71643, filed on Nov. 29, 2000; 2001-33142, filed on Jun. 13, 2001; and 2001-67901, filed on Nov. 1, 2001, and parent U.S. patent application Ser. No. 09/995,798, filed Nov. 29, 2001, are incorporated herein in their entirety by reference.

In accordance with an embodiment of the present invention, Cu-containing catalysts stabilized with silica are applied to a hydrogenation process for preparing a 1,3-alkandiol from a 3-hydroxyester. The primary component of the catalysts is Cu in the form of an oxide, (e.g., CuO) and the weight ratio of the copper oxide (CuO) to silica ($SiO_2$) in the catalyst is within the range of from about 95:5 to about 50:50. The silica-stabilized copper oxide catalysts can generally be represented by CuO—$SiO_2$. However, the conventional CuO—$SiO_2$ catalysts prepared by impregnating a conventional silica carrier with copper oxide, for example, as described in U.S. Pat. No. 4,511,744, is inadequate for the hydrogenation process of the present invention. To secure high catalytic activity required in the present invention, the CuO—$SiO_2$ catalyst should be prepared in a particular manner in the present invention wherein micro-particles (diameter $\leq 10$ nm) of the copper oxide precursor are stabilized with silica. That is, the catalyst used in the present invention preferably is prepared by adding an alkaline precipitator to an aqueous copper salt solution, and then aging the resulting copper hydroxide particles in the presence of a colloidal silica. As an alkaline precipitator, a carbonate or a bicarbonate of Group 1 metals, such as Na, K, Li, Rb and Cs, as well as sodium hydroxide and potassium hydroxide are preferred. Significantly, the silica constituting the catalyst of the present invention functions as an essential component, and thus it is clearly discriminated from the conventional carriers.

Copper salt used in the present invention can be any copper salt useful in forming the catalyst. Particularly preferred examples include copper nitrate, copper chloride, copper acetate and copper sulfate, and preferred concentrations thereof in the aqueous copper salt solution are within the range of from about 5 wt % to about 25 wt %.

Colloidal silica used in the present invention can be made by any of known methods (see: for example, "The Chemistry of Silica," John Wiley & Sons, Inc., New York, 1979, pp. 331~334). Also, commercially available products such as Ludox AS (DuPont, 30 wt % to 40 wt % of silica), Snowtex (Nissan Chemical Industry, 30 wt % to 40 wt % of silica), SILIFOG (Acehitech, 30 wt % to 40 wt % of silica), and so on, also can be used in the present invention.

According to the present invention, the hydrogenation catalyst may further comprise one or more promoters in order to improve its hydrogenation activity or selectivity.

Preferred promoters can be exemplified by Re, Ru, Pd, Pt, Rh, Ag, Se, Te, Mo and Mn, and their content in the catalyst preferably is within the range of from about 0.001 to about 10 mol %, more preferably from about 0.003 to about 7 mol %, based on Cu.

The catalyst of the present invention can be formed by any of known methods including the conventional extruding method, pelleting method, and impregnating method using thermal-resistant carriers. The catalyst thus formed then can be calcined at between about 200° C. to about 800° C., preferably between about 300° C. to about 700° C., for between about 2 to about 10 hrs. Those skilled in the art are capable of preparing the catalyst of the invention using the guidelines provided herein.

The calcined catalyst preferably is in the form of an oxide, and therefore, it should be activated prior to use, preferably by reduction with hydrogen or a hydrogen-containing gas at between about 100° C. to about 250° C. for between about 1 hr to about 60 hrs. In general, this activation procedure can be performed while flowing the hydrogen or hydrogen-containing gas diluted with nitrogen or argon gas into a reactor filled with the calcined oxide catalyst in the presence of an appropriate organic solvent. There are, however, apprehensions about catalyst degradation by heat generated in the course of reduction when carrying out this activation procedure. The present invention aims to prevent the catalyst from being degraded during reduction as well as from being converted into an undesired form, by reducing the catalyst in the presence of a specific activation solvent. Based on the catalyst so formed, the following hydrogenation step may be carried out in a liquid phase slurry. Thus, the activation of the catalyst according to the present invention can be achieved with greater efficiency than that of the conventional liquid-gas phase or gas phase method. In the activation of the catalyst, the pressure of the hydrogen or hydrogen-containing gas preferably is maintained between about 5 psig to about 2000 psig.

Any activation solvent can be used in the invention so long as it is capable of providing the above-described desirable effects. Preferred examples of the activation solvent include high boiling point solvents such as tetraethyleneglycoldimethylether (hereinafter, referred to as "TEGDME"), pentaethyleneglycoldimethylether and sulfolane, as well as low boiling point solvents such as pentane, hexane, 1,4-dioxane and methanol.

The activation solvent may be removed by filtration and/or washing prior to the following hydrogenation of 3-hydroxyesters, or alternatively, may be mixed with a reaction solvent used in the hydrogenation reaction without further treatment. Where the activation solvent and the reaction solvent are mixed together, the mixing ratio of the former to the latter preferably is between about 5:95 and 90:10(w/w).

According to the present invention, the hydrogenation catalyst may be used after modification with an alkylsilane compound in order to improve its catalytic activity and selectivity. At this time, hydroxyl groups of silica in the catalyst preferably are masked with the alkylsilane compound, whereby the hydrophilic catalyst becomes hydrophobic. As the alkylsilane compound, trialkoxymonoalkylsilane, dialkoxydialkylsilane or monoalkoxytrialkylsilane can be used, wherein the alkyl group preferably consists of 1 to 30 carbon atoms, and the alkoxy group is a $C_{1-5}$ linear or non-linear alkoxy group, preferably a methoxy or ethoxy group. Such alkylsilane compounds can be exemplified by trimethoxypropylsilane, trimethoxyoctylsilane, dimethoxydimethylsilane, dimethoxymethylpropylsilane, dimethoxymethyloctylsilane, methoxytrimethylsilane, methoxydimethylpropylsilane and methoxydimethyloctylsilane.

3-hydroxyesters used as a substrate in the hydrogenation reaction according to the present invention preferably are represented by the following formula (I):

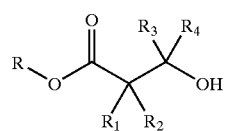

(I)

in the above formula (I),
each of $R_1$, $R_2$, $R_3$, $R_4$ and R, independently, is a hydrogen atom, a $C_{1\sim 20}$ non-branched saturated aliphatic hydrocarbon, branched saturated aliphatic hydrocarbon, saturated cyclic hydrocarbon or ring-containing aliphatic hydrocarbon, or a hydrocarbon derived from substitution of ester, hydroxyl and/or alkoxy groups for hydrogen atoms at one or more carbon chains of any of the aforementioned $C_{1\sim 20}$ hydrocarbon species. In the above formula (I), R of the ester group preferably is methyl, ethyl, n-propyl, isopropyl, n-butyl, isobutyl, t-butyl, cyclohexyl, or cyclohexane methyl.

Preferred examples of the 3-hydroxyesters useful in the present invention include, but are not limited to methyl (or ethyl) 3-hydroxypropionate, 3-hydroxybutyric ester, 3-hydroxypentanoic ester, 3-hydroxyheptanoic ester, 3-hydroxyoctanoic ester, 3-hydroxynonanoic ester, 3-hydroxydecanoic ester, 2-methyl-3-hydroxypropanoic ester, 2-methyl-3-hydroxybutanoic ester, 2-methyl-3-hydroxypentanoic ester, 2-methyl-3-hydroxyhexanoic ester, 2-methyl-3-hydroxyheptanoic ester, 2-methyl-3-hydroxyoctanoic ester, 2-methyl-3-hydroxynonanoic ester, 2-methyl-3-hydroxydecanoic ester, 2-ethyl-3-hydroxybutanoic ester, 2-ethyl-3-hydroxypentanoic ester, 2-ethyl-3-hydroxyhexanoic ester, 2-ethyl-3-hydroxyheptanoic ester, 2-ethyl-3-hydroxyoctanoic ester, 2-ethyl-3-hydroxynonanoic ester, and 2-ethyl-3-hydroxydecanoic ester.

The process for preparing 1,3-alkandiols from 3-hydroxyesters by using the hydrogenation catalyst according to the present invention is characterized in that hydrogenation of 3-hydroxyesters is carried out in a liquid phase slurry. In the liquid phase slurry method according to the present invention, the catalyst is not immobilized to form a layer unlike in the conventional gas phase and liquid-gas phase methods. Instead, the catalyst of the present invention exists in the form of slurry and consequently has ready contact with hydrogen and the substrate dissolved in a reaction solvent, and therefore catalyzes the hydrogenation reaction vigorously. The hydrogenation reaction according to this liquid phase slurry method of the present invention provides advantages unexpected from the conventional gas phase and liquid-gas phase methods. Namely, the conventional gas phase and liquid-gas phase methods are limited to increasing the selectivity for 1,3-alkanediols beyond 90%, whereas the present invention can easily achieve high selectivity for 1,3-alkanediols greater than 90%, preferably amounting to 100%. The selectivity of the catalyzed reaction of the present invention can be increased to greater than 90% by controlling overall reaction conditions including concentration of the reactant and pressure of the hydrogen gas. Those skilled in the art will understand that the present invention is not limited to catalyzed reactions having a selectivity greater than 90%.

In order to produce 1,3-alkandiols in a high yield, it is desired that there be a high selectivity for 1,3-alkandiols notwithstanding a low conversion rate. This is due to that if selectivity for 1,3-alkanediols is high in spite of low conversion rate, then unreacted, i.e., remnant, 3-hydroxyesters can be separated and recycled to the hydrogenation reaction. Such recycling significantly increases the efficiency of use of the reactant. On the other hand, even if the conversion rate is high, a low selectivity for 1,3-alkanediols results in side products rather than the desired 1,3-alkanediols, and consequently, the overall reaction efficiency decreases.

Further, use of the liquid phase slurry method of the present invention can greatly improve both the conversion rate and the selectivity, while using much lesser hydrogen than used in the conventional liquid-gas phase or gas phase method. Moreover, the conventional liquid-gas phase and gas phase methods have been known to have disadvantages in that lactone is inevitably generated at a high concentration of the reactant, whereas the liquid phase slurry method of the present invention produces little lactone. As a consequence, cumbersome separation of lactone and environmental pollution caused by toxic side products generated therefrom can be avoided.

According to the present invention, 3-hydroxyesters can be supplied to the hydrogenation reaction as dissolved in an alcohol solvent or in a mixed solvent consisting of an alcohol and a high-boiling point solvent that boils at a higher temperature than the reactant and product do. The 3-hydroxyesters are supplied in this manner for the following purposes: (i) suppressing side reactions including lactonization and condensation reactions between the reactant, 3-hydroxyester, itself as well as between the reactant and the product, (ii) enhancing catalytic activity and selectivity of the catalyst by controlling the concentration of the reactant to contact the catalyst during the reaction; and (iii) relieving significant decrease of selectivity of the catalyst at a high conversion rates. Thus, 3-hydroxyesters preferably are dissolved in the alcohol or a mixed solvent at a concentration within the range of from about 2~98 wt %.

The alcohol solvent used in the hydrogenation reaction according to the present invention is not specifically limited, but $C_{1\sim 5}$ linear or non-linear alcohols, such as methanol, ethanol, propanol, isopropanol, n-butanol, isobutanol, t-butanol and so on, are preferred, considering that easy separation and purification of the reaction product from the solvent. As the high-boiling point solvent optionally used in conjunction with the alcohol solvent, any solvent can be used, provided that it can be readily mixed with 3-hydroxyesters and has a boiling point higher than that of 1,3-alkanediols so that it can be readily separated therefrom. Preferably, ethers, such as TEGDME, pentaethyleneglycoldimethylether and sulfolane, are used. It is preferred in the invention that the mixing ratio of the alcohol to the high boiling point solvent preferably is between about 5:95 and about 90:10(w/w).

In the hydrogenation reaction according to the present invention, the reaction temperature preferably is adjusted to be within the range of from about 100~250° C., more preferably from about 120~200° C., and the reaction pressure preferably is within the range of from about 50~3,000 psig, more preferably from about 150~2,000 psig.

The present invention can be more clearly understood with referring to the following examples. It should be understood that the following examples are not intended to restrict the scope of the present invention in any manner.

EXAMPLE 1

To a solution containing 60.0 g of [Cu(NO$_3$)$_2$.3H$_2$O] and 2.54 g of [Mn(NO$_3$)$_2$.6H$_2$O] in 400 ml of distilled water were added 129 ml of aqueous NaOH solution (16 wt %) to form co-precipitates. The co-precipitates were allowed to age at 70~80° C. for 4 hrs, following addition of 12.8 g of aqueous colloidal silica, Ludox AS-40 (ammonium-stabilized type, 40 wt % of silica), to the solution. The resulting slurry was recovered by filtration, followed by washing with distilled water, and drying at 120° C. for 12 hrs. Then, the dry powder was shaped by pressing and crushed again into particles having 20~40 mesh size. The particles were calcined at 450° C. under atmosphere for 6 hrs to produce a CuO(77 wt %)-SiO$_2$(20 wt %)-MnO$_2$(3 wt %) catalyst.

EXAMPLE 2

To a 600 ml high pressure reactor were sequentially added 5.0 g of the CuO(77 wt %)-SiO$_2$(20 wt %)-MnO$_2$(3 wt %) catalyst obtained from the above Example 1 and 250 ml of tetraethyleneglycoldimethylether (TEGDME) as an activation solvent. Subsequently, 5% H$_2$/N$_2$ mixed gas was flowed into the reactor to a pressure of 500 psig, and the temperature in the reactor was elevated to 180° C., where reduction of the catalyst was continued for 20 hrs, to produce an activated catalyst.

The activated catalyst was recovered and washed several times with methanol under nitrogen gas atmosphere. To 5.0 g of the washed catalyst were then added 5.0 g of 3-hydroxymethyl propionate (HPM) and 350 ml of methanol as a reaction solvent, and the hydrogenation reaction was carried out for 20 hrs at 150° C. under a pressure of 1450 psig. The resulting product was collected into a sampling tube and subjected to GC analysis. The result is set forth in Table 1.

EXAMPLE 3

The CuO(77 wt %)-SiO$_2$(20 wt %)-MnO$_2$(3 wt %) catalyst obtained from the above Example 1 was activated through reduction according to the same manner as in the above Example 2, except that the reduction was continued for 2 hrs.

The activated catalyst was recovered and washed several times with methanol under nitrogen gas atmosphere. To 10.0 g of the washed catalyst were then added 10.0 g of HPM and 300 ml of methanol as a reaction solvent, and the hydrogenation reaction was carried out for 15 hrs at 150° C. under a pressure of 1450 psig. The resulting product was collected into a sampling tube and subjected to GC analysis. The result is set forth in Table 1.

EXAMPLE 4

The CuO(77 wt %)-SiO$_2$(20 wt %)-MnO$_2$(3 wt %) catalyst obtained from the above Example 1 was activated through reduction according to the same manner as in the above Example 2, except that the reduction was continued for 44 hrs.

The activated catalyst was recovered and washed several times with methanol under nitrogen gas atmosphere. To 10.0 g of the washed catalyst were then added 10.0 g of HPM and 250 ml of methanol as a reaction solvent, and the hydrogenation reaction was carried out for 20 hrs at 150° C. under a pressure of 1450 psig. The resulting product was collected into a sampling tube and subjected to GC analysis. The result is set forth in Table 1.

TABLE 1

| | Activation time (h) | Activation solvent (ml) | Reaction time (h) | Reaction temperature (° C.) | Reaction solvent (ml) | Reaction pressure (psig) | Conversion rate (%) | Selectivity 13PD[1] | 1PO[2] | MP[3] |
|---|---|---|---|---|---|---|---|---|---|---|
| Example 2 | 20 | 250 | 20 | 150 | 350 | 1450 | 90.92 | 100 | 0 | 0 |
| Example 3 | 2 | 250 | 15 | 150 | 300 | 1450 | 64.13 | 86.32 | 3.77 | 9.9 |
| Example 4 | 44 | 250 | 15 | 150 | 250 | 1450 | 60.44 | 82.07 | 3.03 | 14.9 |
| | 44 | 250 | 20 | 150 | 250 | 1450 | 83.75 | 84.61 | 3.07 | 12.32 |

[1] 13PD: 1,3-propandiol
[2] 1PO: 1-propanol
[3] MP: methylpropionate

EXAMPLE 5

To a 600 ml high pressure reactor was sequentially added 5.0 g of the CuO(77 wt %)-SiO$_2$(20 wt %)-MnO$_2$(3 wt %) catalyst obtained from the above Example 1 and 250 ml of tetraethyleneglycoldimethylether (TEGDME) as an activation solvent. Subsequently, 5% H$_2$/N$_2$ mixed gas was flowed into the reactor to a pressure of 500 psig, and temperature in the reactor was elevated to 180° C., where reduction of the catalyst was continued for 20 hrs, to produce an activated catalyst.

The activated catalyst was recovered and washed several times with methanol under nitrogen gas atmosphere. To 5.0 g of the washed catalyst were then added 5.0 g of 3-hydroxymethyl propionate (HPM) and 350 ml of methanol as a reaction solvent, and the hydrogenation reaction was carried out for 4 hrs at 150° C. under a pressure of 1450 psig. The resulting product was collected into a sampling tube and subjected to GC analysis. The result is set forth in Table 2.

EXAMPLE 6

To a 600 ml high pressure reactor were sequentially added 10.0 g of the CuO(77 wt %)-SiO$_2$(20 wt %)-MnO$_2$(3 wt %) catalyst obtained from the above Example 1 and 250 ml of tetraethyleneglycoldimethylether (TEGDME) as an activation solvent. Subsequently, 5% H$_2$/N$_2$ mixed gas was flowed into the reactor to a pressure of 500 psig, and temperature in the reactor was elevated to 180° C., where reduction of the catalyst was continued for 2 hrs, to produce an activated catalyst.

The activated catalyst was recovered and washed several times with methanol under a nitrogen gas atmosphere. To 10.0 g of the washed catalyst were then added 5.0 g of 3-hydroxymethyl propionate (HPM) and 300 ml of methanol as a reaction solvent, and the hydrogenation reaction was carried out for 2 hrs at 150° C. under a pressure of 1450 psig. The resulting product was collected into a sampling tube and subjected to GC analysis. The result is set forth in Table 2.

EXAMPLE 7

The procedure of Example 7 was conducted according to the same manner as in the above Example 6, except that the reduction of the catalyst was continued for 44 hrs and the hydrogenation reaction was continued for 3 hrs while using 250 ml of methanol as the reaction solvent. The resulting product was collected into a sampling tube and subjected to GC analysis. The result is set forth in Table 2.

EXAMPLE 10

To a 600 ml high pressure reactor were sequentially added 20.0 g of the CuO(77 wt %)-SiO$_2$(20 wt %)-MnO$_2$(3 wt %) catalyst obtained from the above Example 1 and 200 ml of tetraethyleneglycoldimethylether (TEGDME) as an activation solvent. Subsequently, H$_2$ gas was flowed into the reactor to a pressure of 1000 psig, and the temperature in the reactor was elevated to 180° C., where reduction of the catalyst was continued for 40 hrs to provide an activated catalyst.

Without washing, to the activated catalyst in TEGDME were added 10.0 g of 3-hydroxymethyl propionate (HPM) and 200 ml of methanol as a reaction solvent, and the hydrogenation reaction was carried out at 165° C. under a pressure of 1450 psig, while increasing the reaction time up to 18 hrs. The resulting product was collected into a sampling tube and subjected to GC analysis. The result is set forth in Table 4. Meanwhile, the catalyst was recovered from the reaction mixture, followed by washing with methanol and air-drying for further use.

TABLE 2

| | Activation time (h) | Activation solvent (ml) | Reaction time (h) | Reaction temperature (° C.) | Reaction solvent (ml) | Reaction pressure (psig) | Conversion rate (%) | Selectivity 13PD | 1PO | MP |
|---|---|---|---|---|---|---|---|---|---|---|
| Example 5 | 20 | 250 | 4 | 150 | 350 | 1450 | 31.63 | 100 | 0 | 0 |
| Example 6 | 2 | 250 | 2 | 150 | 300 | 1450 | 12.65 | 95.38 | 0 | 4.62 |
| Example 7 | 44 | 250 | 3 | 150 | 250 | 1450 | 21.07 | 93.55 | 0 | 6.33 |

EXAMPLE 8

To a 600 ml high pressure reactor were sequentially added 10.0 g of the CuO(77 wt %)-SiO$_2$(20 wt %)-MnO$_2$(3 wt %) catalyst obtained from the above Example 1 and 250 ml of tetraethyleneglycoldimethylether (TEGDME) as an activation solvent. Subsequently, H$_2$ gas was flowed into the reactor to a pressure of 1000 psig, and the temperature in the reactor was elevated to 180° C., where reduction of the catalyst was continued for 4 hrs, to produce an activated catalyst.

Without washing, to the activated catalyst in TEGDME were added 10.0 g of 3-hydroxymethyl propionate (HPM) and 200 ml of methanol as a reaction solvent, and the hydrogenation reaction was carried out for 16 hrs at 165° C. under a pressure of 1450 psig. The resulting product was collected into a sampling tube and subjected to GC analysis. The result is set forth in Table 3.

EXAMPLE 9

The procedure of Example 9 was conducted in the same manner as in the above Example 8, except that the hydrogenation reaction was carried out at 150° C. The resulting product was collected into a sampling tube and subjected to GC analysis. The result is set forth in Table 3.

EXAMPLE 11

Using the catalyst recovered from the above Example 10, the hydrogenation reaction was conducted according to the same manner as in the above Example 10. The resulting product was collected into a sampling tube and subjected to GC analysis. The result is set forth in Table 4.

TABLE 3

| | Activation time (h) | Activation solvent | Reaction time (h) | Reaction temperature (° C.) | Reaction solvent | Reaction pressure (psig) | Conversion rate (%) | Selectivity 13PD | 1PO | MP |
|---|---|---|---|---|---|---|---|---|---|---|
| Example 8 | 4 | TEGDME | 16 | 165 | TEGDME/methanol | 1450 | 60.43 | 91.43 | 0 | 8.59 |
| Example 9 | 4 | TEGDME | 16 | 150 | TEGDME/methanol | 1450 | 21.60 | 100 | 0 | 0 |

TABLE 4

| | Reaction time (h) | Reaction temperature (° C.) | Reaction solvent | Reaction pressure (psig) | Conversion rate (%) | Selectivity for 13PD (%) |
|---|---|---|---|---|---|---|
| Example 10 | 8 | 165 | TEGDME/methanol | 1450 | 43.39 | 97 |
| | 10 | | | | 53 | 95 |
| | 12 | | | | 60 | 95 |
| | 14 | | | | 68 | 94 |
| | 16 | | | | 76 | 92 |
| | 18 | | | | 80.68 | 91.08 |
| Example 11 | 0 | 165 | Methanol | 1450 | 0 | 0 |
| | 2 | | | | 10.25 | 96 |
| | 6 | | | | 31.06 | 94 |
| | 14 | | | | 72.09 | 92 |
| | 18 | | | | 80.92 | 87 |

As stated above, by virtue of the present invention, it is possible to selectively prepare a 1,3-alkanediol from a 3-hydroxyester in a high yield.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the invention as set forth in the following claims.

What is claimed is:

1. A process for preparing a 1,3-alkandiol from a 3-hydroxyester, comprising:

A) preparing a catalyst by adding an alkaline precipitator to an aqueous copper salt solution to form copper hydroxide particles, and aging the particles following the addition of a colloidal silica thereto;

B) activating the catalyst by reduction using a $H_2$ gas or a $H_2$-containing gas and applying a pressure within the range of from about 5 psig to about 2000 psig at a temperature within the range of from about 100° C. to about 250° C. in the presence of an activation solvent to prepare an activated catalyst; and C) hydrogenating a 3-hydroxyester in a liquid phase slurry with a $H_2$ gas or a $H_2$-containing gas and applying a pressure within the range of from about 50 psig to about 3000 psig at a temperature within the range of from about 100° C. to about 250° C. in the presence of the activated catalyst and a reaction solvent to prepare the 1,3-alkandiol.

2. The process as claimed in claim 1, wherein the alkaline precipitator is an alkali metal carbonate, an alkali metal bicarbonate, sodium hydroxide or potassium hydroxide.

3. The process as claimed in claim 1, wherein the aqueous copper salt solution is an aqueous solution containing from about 5 wt % to about 25 wt % of at least one copper compound selected from the group consisting of copper nitrate, copper chloride, copper acetate, copper sulfate, and mixtures thereof.

4. The process as claimed in claim 1, wherein the catalyst comprises CuO to $SiO_2$ in a weight ratio of CuO to $SiO_2$ of between about 95:5 and about 50:50.

5. The process as claimed in claim 1, wherein the catalyst further comprises one or more promoters selected from the group consisting of Re, Pd, Ru, Pt, Rh, Ag, Se, Te, Mo, Mn, and mixtures thereof, in an amount of from about 0.001 mol % to about 10 mol % based on Cu.

6. The process as claimed in claim 1, wherein the 3-hydroxyester is represented by the formula (I):

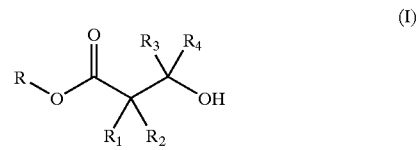

(I)

wherein each of $R_1$, $R_2$, $R_3$, $R_4$ and R, independently, is a hydrogen atom, a $C_{1\sim20}$ non-branched saturated aliphatic hydrocarbon, branched saturated aliphatic hydrocarbon, saturated cyclic hydrocarbon or ring-containing aliphatic hydrocarbon, or a hydrocarbon derived from substitution of ester, hydroxyl and/or alkoxy groups for hydrogen atoms at one or more carbon chains of any of said $C_{1\sim20}$ hydrocarbon species.

7. The process as claimed in claim 6, wherein R is selected from the group consisting of methyl, ethyl, n-propyl, isopropyl, n-butyl, isobutyl, t-butyl, cyclohexyl, and cyclohexane methyl.

8. The process as claimed in claim 1, wherein the activation solvent is at least one high boiling point solvent selected from the group consisting of tetraethyleneglycoldimethylether, pentaethyleneglycoldimethylether, sulfolane, and mixtures thereof.

9. The process as claimed in claim 1, wherein the activation solvent is at least one low boiling point solvent selected from the group consisting of pentane, hexane, 1,4-dioxane, and methanol.

10. The process as claimed in claim 1, wherein the procedure C) is carried out without removing the activation solvent from the catalyst activated in procedure B).

11. The process as claimed in claim 10, wherein the mixing ratio of the activation solvent to the reaction solvent is within the range of from about 5:95 to about 90:10(w/w).

12. The process as claimed in claim 1, wherein procedure C) is carried out after removing the activation solvent from the catalyst activated in procedure B).

13. The process as claimed in claim 1, wherein the reaction solvent used in procedure C) is an alcohol solvent, or a mixed solvent comprising an alcohol and a high-boiling point solvent that boils at a temperature higher than the boiling point of 1,3-alkandiol.

14. The process as claimed in claim 13, wherein the alcohol solvent is at least one solvent selected from the group consisting of methanol, ethanol, propanol, isopropanol, n-butanol, isobutanol, t-butanol, and mixtures thereof.

15. The process as claimed in claim 13, wherein the high-boiling point solvent is at least one solvent selected from the group consisting of tetraethyleneglycoldimethylether, pentaethyleneglycoldimethylether, sulfolane, and mixtures thereof, and wherein the mixing ratio of the alcohol solvent to the high-boiling point solvent is within the range of from about 5:95 to about 90:10 (w/w).

16. The process as claimed in claim 1, further comprising:

D) recovering remnant 3-hydroxyester from the hydrogenation reaction mixture at the end of procedure C) and repeating procedure C) by using the recovered 3-hydroxyester.

* * * * *